United States Patent [19]

Schlosser

[11] 3,935,260

[45] Jan. 27, 1976

[54] AUTO-CONDENSATION PRODUCTS OF UREA

[75] Inventor: Fritz Dieter Schlosser, Germiston, South Africa

[73] Assignee: African Explosives & Chemical Industries Limited, Transvaal, South Africa

[22] Filed: Oct. 18, 1973

[21] Appl. No.: 407,512

Related U.S. Application Data

[63] Continuation of Ser. No. 190,273, Oct. 18, 1971, abandoned.

[30] Foreign Application Priority Data

Oct. 21, 1970  South Africa.................. 70/7156

[52] U.S. Cl................ 260/553 B; 426/69; 426/807
[51] Int. Cl.$^2$..................................... C07C 127/24
[58] Field of Search......... 426/69; 260/553 B; 71/28

[56] References Cited
UNITED STATES PATENTS

| | | | |
|---|---|---|---|
| 2,145,392 | 1/1939 | Harmon | 260/553 B |
| 2,370,065 | 2/1945 | Olin | 260/553 B |
| 2,524,049 | 10/1950 | Garbo | 260/553 B |
| 2,768,895 | 10/1956 | Kamlet | 260/553 B |

FOREIGN PATENTS OR APPLICATIONS 1,156,099  6/1969  United Kingdom............. 260/553 B

OTHER PUBLICATIONS

Hackh's Chemical Dictionary, 4th Ed., Grant, McGraw–Hill, N.Y., 1969, p. 650.
Chem. Abstracts, Vol. 67, 1967, 108269s.

*Primary Examiner*—Norman Yudkoff
*Assistant Examiner*—Hiram H. Bernstein
*Attorney, Agent, or Firm*—Cushman, Darby & Cushman

[57] ABSTRACT

Process for producing a mixture of auto-condensation products of urea containing predominantly biuret suitable as a non-protein nitrogen supplement for ruminant feeds comprising heating with continuous stirring in a reaction vessel, having a smooth surface, finely divided urea dispersed in an inert liquid containing a surface active agent in an amount of from 0.01 to 1.0 per cent m/m of the initial quantity of urea at a temperature between 125°C and 180°C for a period of time sufficient to convert at least 90 per cent of the urea substantially into the mixture and separating the particles of the mixture thus formed from the inert liquid to recover the mixture as a particulate product.

19 Claims, No Drawings

AUTO-CONDENSATION PRODUCTS OF UREA

This is a continuation of application Ser. No. 190,273 filed Oct. 18, 1971, and now abandoned.

This invention relates to auto-condensation products of urea suitable for use as non-protein nitrogen supplements for ruminant feeds.

Auto-condensation products of urea as non-protein nitrogen supplements for ruminant feed have been used for some time. The advantage of using urea auto-condensation products instead of urea is that the risk of toxic after effects in ruminants is greatly reduced.

Urea auto-condensation products in which biuret is the predominant component have proved to be particularly useful as non-protein nitrogen supplements for ruminant feed. Such products are prepared by heating urea under controlled temperature conditions to minimise the formation of less desirable auto-condensation products. It is, however, difficult to obtain the desired product containing predominantly biuret in a good yield using a one step process. Therefore, a second step has to be introduced in which the desired product is obtained by crystallisation from an aqueous solution of the product of the first step to obtain a supplement for ruminant feed containing between 60 and 90 per cent biuret.

The nitrogen content of products containing ammelide and large amounts of cyanuric acid are lower than those containing predominantly biuret. Ammeline and melamine are known to be unacceptable to ruminants in concentrations above 5 per cent by weight of the feed supplement and it is extremely difficult to control the formation of these and other less desirable products when heating urea.

An object of the present invention is to provide a process for the manufacture of auto-condensation products of urea in a particulate form containing predominantly biuret suitable for an animal feed, which avoids the difficulties encountered in the conventional manufacture of urea auto-condensation products.

Another object is to obtain a high level of nitrogen content in the auto-condensation products of the process to improve their feed supplement value.

According to the present invention we provide a process for producing a mixture of auto-condensation products of urea containing predominantly biuret suitable as a non-protein nitrogen supplement for ruminant feeds comprising heating with continuous stirring in a reaction vessel, having a smooth surface, finely divided urea dispersed in an inert liquid containing a surface active agent in an amount of from 0.01 to 1.0 per cent m/m of the initial quantity of urea at a temperature between 125°C and 180°C for a period of time sufficient to convert at least 90 per cent of the urea substantially into the mixture and separating the particles of the mixture thus formed from the inert liquid to recover the mixture as a particulate product.

If desired, the mixture of urea auto-condensation products may be cooled while stirring before the particulate product is finally separated from the inert liquid.

The product obtained from the process of the invention contains 10 per cent or less unconverted urea and can, after a final treatment if required to remove traces of inert liquid, be used as a non-protein supplement for ruminant feed without further purification steps.

It has been determined that the surfactants remaining in the product are not toxic to the rumen microbes as is illustrated by the following tests wherein surfactants in amounts well beyond those found in the product of the process are proved to be harmless.

Rumen fluid was taken from fistulated sheep and incubated for 20–30 minutes with surfactants at a concentration of 0.4 mg per 100 ml rumen fluid or 4.2 mg per 100 ml rumen fluid. These concentrations are respectively one and ten times those to be expected if a ruminant consumed a normal amount of the product. After 20–30 minutes the rate of gas evolution by rumen mibrobes was determined. This rate was proportional to the number of rumen microbes present and a diminution as compared with untreated rumen fluid indicated that some microbes had been killed. The results of four experiments are given in the Table below. They show that no reduction in rumen microbes occurred at 10 times the expected concentration of surfactants in rumen fluid.

TABLE

Rates of gas evolution from rumen fluid expressed as a percentage of the rate from untreated rumen fluid

| Treatment | | | Rate (% of untreated) |
|---|---|---|---|
| Expt 1 | Surfactants | 0,4 mg % | 100,0 |
| | " | 4,2 mg % | 107,8 |
| Expt 2 | " | 0,4 mg % | 107,3 |
| | " | 4,2 mg % | 105,5 |
| Expt 3 | " | 0,4 mg % | 95,2 |
| | " | 4,2 mg % | 114,3 |
| Expt 4 | " | 0,4 mg % | 105,6 |
| | " | 4,2 mg % | 106,4 |
| Control* | 25% microbial kill | | 80,6 |
| | 50% microbial kill | | 59,5 |

*The control shows that, when one quarter of the bacteria is killed, the rate drops to 80,6% and, when half is killed, the rate drops to 59,5%. No such drops in rate were observed to occur from adding the surfactants.

The inert liquid used in carrying out the process of the invention should, preferably, be such that the solubility therein of the urea or its auto-condensation products at ambient temperature is not more than 5 per cent by weight of the urea or such products. Further, the liquid should not react with urea or its auto-condensation products. It is preferred to use a liquid having a boiling point of between 150° and 180°C to facilitate temperature control of the urea auto-condensation reaction by boiling the liquid under reflux at atmospheric pressure.

It is further preferred that the inert liquids have a low mammalian toxicity to avoid additional purification of the products. Also, it is convenient to use inert liquids having a narrow boiling range so that the liquids may be removed to the greatest extent by drying at elevated temperatures.

The preferred liquids are branched chain paraffins having suitable boiling ranges, which are substantially non-toxic and which may be removed by drying without leaving residues in the product.

However, other liquids may be used such as, for example, chlorinated aromatic compounds and substituted aromatic compounds.

The surface active agents may be any suitable surface active agent or mixture of surface active agents. Suitable surface active agents are, for example:

a. Cationic surface active agents such as quaternary ammonium salts, particularly N-tetradecyl dimethyl benzyl ammonium chloride and N-alkyl)C-$_{16}$–C$_{18}$) benzyl dimethyl ammonium chloride.

b. Anionic surface active agents such as paraffinic sulphonates.
c. Non-ionic surface active agents such as nonyl phenyl ethylene oxide.

Mixtures containing (a) and (b) may be used advantageously in that these mixtures tend to reduce frothing of the reaction mass and reduce the microbial toxicity of (a).

The preferred surface active agents are those having low mammalian and microbial toxicity at the concentrations used in the process to avoid elaborate purification of the product.

The amount of surface active agent present in the reaction mixture may be between, 0.01 and 1.0 per cent by mass of the total mass of urea and liquid.

It was found that a smooth, round bottomed vessel gave the most uniform particle size of product. The reaction is preferably carried out in glass, glass-lined or vitreous enamel-lined vessels to avoid adherance of the urea or urea auto-condensation products to the walls of the vessels.

Accordingly, the expression "smooth surface" as used in this specification means a surface adapted to avoid a condition of stickiness when contacted by urea and its auto-condensation products.

The reaction is normally carried out at atmospheric pressure. However, when liquids are used having boiling points above 200°C or below 150°C, subatmospheric or superatmospheric pressures may be used to decrease or increase the boiling points of these liquids.

In carrying out the process according to the invention, the mixture of urea, inert liquid and surface active agent is heated while stirring to a temperature of between 125°C and 180°C, preferably the boiling point of the liquid under reflux at atmospheric pressure. The rate of removal of ammonia formed by the reaction is considerably enhanced if a boiling liquid is used. The reaction mixture is kept at this temperature until at least 90 per cent of the urea has been converted into the preferred urea auto-condensation products.

It has been found that under the conditions of the process of the invention, the urea is selectively converted into biuret with the formation of only minor amounts of other auto-condensation products such as cyanuric acid, triuret and ammelide.

The period of time required to effect the conversion depends on the temperature used and, at a temperature of about 170°C, the reaction period is approximately a little longer than one hour.

The reaction mass is then cooled while stirring which causes the granules or prills of the urea auto-condensation products and unconverted urea to harden, after which they can be separated easily from the inert liquid by, for example, filtration. The inert liquid may be recycled to the process without any purification steps.

The particulate material may be treated to remove any traces of inert liquid, which may adhere to the material, or the material can be used as a non-protein nitrogen supplement for ruminant feed without such treatment.

The following Examples illustrate the invention, without limiting the scope of the invention thereto. In the Examples all percentages are expressed as mass percentage.

EXAMPLE I

A mixture of 200 cm³ of a branched chain paraffin, sold under the Esso trade name "Isopar" H, and 0.2 g surface active agent, comprising 0.1 g myristyl dimethyl benzyl ammonium chloride and 0.1 g sodium dodecyl benzene sulphonate, was heated in a glass vessel to boiling under reflux. The boiling range of the paraffin was 168°-172°C at ambient atmospheric pressure.

100 g of urea was added to the boiling liquid while stirring. The reaction mass was kept at the boiling temperature for 1 hour while stirring. After about 1 hour 20 minutes the formed pyrolysis products started to agglomerate into particles having a diameter of between 1 and 3 mm. After 2 hours, the reaction mass was allowed to cool while stirring. The particulate product was then separated from the liquid by filtration and dried at 100°C for 3 hours to remove the residual liquid.

The recovered liquid could be used again without any treatment such as distillation or washing.

The product was substantially free of liquid and had a total nitrogen content of 37.7%.

The results of the analyses of the product were:

| | |
|---|---|
| Urea | 3,7% |
| Biuret | 46,3% |
| Cyanuric acid | 39,7% |
| Triuret and other insolubles | 9,7% |
| Ammeline | 0,05% |
| Melamine | 0,1% |

EXAMPLE II

The method used was similar to Example I. The following materials were used:
200 cm³ of a branched chain paraffin sold under the Bayer trade name "EC 180" and having a boiling point of 172°C at ambient atmospheric pressure,
0.1 g of a paraffinic sulphonate sold under Farbwerke Hoechst AG trade name "Hostapur" SAS 60,
100 g of urea.

The mixture was kept at boiling point while stirring for a period of 2 hours in a metal vessel, the interior surface of which had a coating of vitreous enamel.

The particulate product obtained was analyzed and the results were as follows:

| | |
|---|---|
| Urea | 4,8% |
| Biuret | 52,9% |
| Cyanuric acid | 32,4% |
| Triuret and other insolubles | 9,6% |
| Ammeline | 0,1% |
| Melamine | 0,1% |
| The total nitrogen content was | 38,3% |

EXAMPLE III

The method used is the same as in Example II. The materials used were:
200 cm³ of a branched chain paraffin sold under the Bayer trade name EC 180, having a boiling point of 172°C at ambient atmospheric pressure.
0.2 g of a mixture of surface active agents used was
0.1 g myristyl dimethyl benzyl ammonium chloride and
0.1 g Hoechst "Hostapur" SAS 60
100 g of urea.

The mixture was kept at boiling point while stirring for a period of 25 minutes.

The particulate product obtained was analyzed and the results were as follows:

| | |
|---|---|
| Urea | 0,9% |
| Biuret | 48,8% |
| Cyanuric acid | 39,7% |
| Triuret and other insolubles | 9,0% |
| Melamine | 0,06% |
| Ammeline | 0,2% |
| The total nitrogen content was | 37,2% |

EXAMPLE IV

The same method was used as in Example III. The materials used were:

200 cm³ branched chain paraffin sold under the Bayer trade name EC 180, having a boiling point of 172°C ambient atmospheric pressure, 0.2 g of a mixture of surface active agents consisting of 0.1 g myristyl dimethyl benzyl ammonium chloride and 0.1 g tridecyl alcohol containing 6 ethoxy groups.

The particulate product obtained was analyzed and the results were as follows:

| | |
|---|---|
| Urea | 1,0% |
| Biuret | 46,1% |
| Cyanuric acid | 41,0% |
| Triuret and other insolubles | 10,0% |
| Ammeline } Melamine } | 0,23% |

The process of the present invention can be operated at comparatively low costs as compared with presently known processes for the manufacture of biuret and the non-protein nitrogen supplement for ruminant feeds produced by this process will not induce toxic after-effects in the ruminants.

This invention includes the auto-condensation products when produced by the process as described herein.

I claim:

1. Process for producing a paruculate mixture of auto-condensation products of urea containing predominantly biuret which is suitable as a non-protein nitrogen supplement for ruminant feeds comprising heating at a temperature between 150°C and 180°C with continuous stirring in a reaction vessel having a smooth surface, finely divided urea dispersed in a non-toxic branched chain paraffin which is inert to urea and its auto-condensation products, has a boiling point in the range of 150° and 180°C and in which urea or its auto-condensation products have a solubility at ambient temperature of not more than 5% by weight of the urea of its auto-condensation products, said paraffin containing a non-toxic surface active agent selected from the group consisting of cationic surface active agents, nonionic surface active agents, anionic surface active agents and mixtures of cationic and anionic surface active agents in an amount of from 0.01 to 1.0 percent m/m of the initial quantity of urea, continuing said heating until at least 90 percent of the urea is converted into said mixture of auto-condensation products and separating the particulate mixture thus formed from the branched chain paraffin.

2. Process as claimed in claim 1 in which the temperature is between 150°C and 175°C and the reaction time is between 25 minutes and 2 hours.

3. Process as claimed in claim 1 or claim 2 in which the paraffin boils at the temperature of heating.

4. Process as claimed in claim 1 in which the branched chain paraffin is polyisobutane.

5. Process as claimed in claim 14 in which the surface active agent is a cationic surface active agent.

6. Process as claimed in claim 1 in which the surface active agent is an anionic surface active agent.

7. Process as claimed in claim 1 in which the surface active agent is a non-ionic surface active agent.

8. Process as claimed in claim 1 in which the surface active agent comprises a mixture of at least one cationic surface active agent and at least one anionic surface active agent.

9. Process as claimed in claim 1 in which the smooth surface of the reaction vessel is a glass surface.

10. Process as claimed in claim 1 in which the smooth surface of the reaction vessel is a vitreous enamel surface.

11. Process as claimed in claim 5 in which the cationic surface active agent is a quaternary ammonium salt.

12. Process as claimed in claim 11 in which the quaternary ammonium salt is N-tetradecyl dimethyl benzyl ammonium chloride or N-alkyl benzyl dimethyl ammonium chloride.

13. Process as claimed in claim 6 in which the anionic surface active agent is a paraffinic sulphonate.

14. Process as claimed in claim 7 in which the non-ionic surface active agent is nonyl phenyl ethylene oxide.

15. Process as claimed in claim 3 in which the heating in the reaction vessel is at subatmospheric pressure.

16. Process as claimed in claim 3 in which the heating in the reaction vessel is at super-atmospheric pressure.

17. Process as claimed in claim 1 in which the mixture is cooled while being stirred to harden the particles before separating the particles from the inert liquid to recover the mixture as a particulate product.

18. Process as claimed in claim 1 in which the inert liquid is recycled to the process without any purification steps.

19. Process as claimed in claim 1 in which the particulate product is treated to remove any traces of inert liquid adhering to the particles.

* * * * *